(12) United States Patent
Chang et al.

(10) Patent No.: US 12,087,444 B2
(45) Date of Patent: Sep. 10, 2024

(54) POPULATION-LEVEL GAUSSIAN PROCESSES FOR CLINICAL TIME SERIES FORECASTING

(71) Applicant: KONINKLIJKE PHILIPS N.V., Eindhoven (NL)

(72) Inventors: Yale Chang, Lincoln, MA (US); Bryan Conroy, Garden City South, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 318 days.

(21) Appl. No.: 17/441,089

(22) PCT Filed: Mar. 18, 2020

(86) PCT No.: PCT/EP2020/057452
§ 371 (c)(1),
(2) Date: Sep. 20, 2021

(87) PCT Pub. No.: WO2020/187987
PCT Pub. Date: Sep. 24, 2020

(65) Prior Publication Data
US 2022/0165417 A1    May 26, 2022

Related U.S. Application Data

(60) Provisional application No. 62/820,408, filed on Mar. 19, 2019, provisional application No. 62/943,955, filed on Dec. 5, 2019.

(51) Int. Cl.
*G16H 50/20* (2018.01)
*G16H 10/60* (2018.01)
(Continued)

(52) U.S. Cl.
CPC ............. *G16H 50/20* (2018.01); *G16H 10/60* (2018.01); *G16H 50/30* (2018.01); *G16H 50/70* (2018.01)

(58) Field of Classification Search
CPC ........ G16H 50/20; G16H 10/60; G16H 50/30; G16H 50/70
See application file for complete search history.

(56) References Cited

U.S. PATENT DOCUMENTS

2013/0116999 A1   5/2013   Stein
2017/0360366 A1*  12/2017  Potes ................. A61M 5/1723
2018/0068083 A1   3/2018   Cohen

FOREIGN PATENT DOCUMENTS

WO    201803646 A1    4/2018

OTHER PUBLICATIONS

Futoma, Joseph, Gaussian Process-Based Models for Clinical Time Series in Healthcare [Doctoral Dissertation, Department of Statistical Science in the Graduate School of Duke University] 2018 (Year: 2018).*

(Continued)

*Primary Examiner* — Meredith A Long

(57) ABSTRACT

A device, system and method for generating a prediction model for a test patient. To generate the prediction model, a multi-dimensional clinical time series for each of a plurality of training patients is collected to generate a training population. A machine learning algorithm is then trained using the training population. Measurement data corresponding to the test patient is also received, the measurement data includes a multi-dimensional clinical time series for the test patient. The test patient is not included in the plurality of training patients. The prediction model is generated for the test patient based on i) the measurement data corresponding to the test patient and ii) training the machine learning algorithm using the training population.

17 Claims, 4 Drawing Sheets

(51) Int. Cl.
  G16H 50/30 (2018.01)
  G16H 50/70 (2018.01)

(56) References Cited

OTHER PUBLICATIONS

Parra, Gabriel & Tobar, Felipe, Spectral Mixture Kernels for Multi-Output Gaussian Processes, 31st Conference on Neural Information Processing Systems, Long Beach, CA, USA, 2017 (Year: 2017).*
International Search Report and Written Opinion, International Application No. PCT/EP2020/057452, Mailed on Jun. 15, 2020.
Rasmussen, Carl Edward. "Gaussian processes in machine learning." In Advanced lectures on machine learning, pp. 63-71. Springer, Berlin, Heidelberg, 2004.
Bonilla, Edwin V., Kian M. Chai, and Christopher Williams. "Multi-task Gaussian process prediction." In Advances in neural information processing systems, pp. 153-160. 2008.
Wilson, Andrew, and Ryan Adams. "Gaussian process kernels for pattern discovery and extrapolation." In International Conference on Machine Learning, pp. 1067-1075. 2013.
Duvenaud, David, James Lloyd, Roger Grosse, Joshua Tenenbaum, and Ghahramani Zoubin. "Structure Discovery in Nonparametric Regression through Compositional Kernel Search." In International Conference on Machine Learning, pp. 1166-1174. 2013.
Wilson, Andrew Gordon, Zhiting Hu, Ruslan Salakhutdinov, and Eric P. Xing. "Deep kernel learning." In Artificial Intelligence and Statistics, pp. 370-378. 2016.
Cheng, Li-Fang, Gregory Darnell, Corey Chivers, Michael E. Draugelis, Kai Li, and Barbara E. Engelhardt. "Sparse Multi-Output Gaussian Processes for Medical Time Series Prediction." arXiv preprint arXiv:1703.09112 (2017).
Schulam, Peter, and Suchi Saria. "A framework for individualizing predictions of disease trajectories by exploiting multi-resolution structure." In Advances in Neural Information Processing Systems, pp. 748-756. 2015.
Futoma, Joseph, Mark Sendak, Blake Cameron, and Katherine Heller. "Predicting disease progression with a model for multivariate longitudinal clinical data." In Machine Learning for Healthcare Conference, pp. 42-54. 2016.
Titsias, Michalis K., and Miguel Lazaro-Gredilla. "Spike and slab variational inference for multi-task and multiple kernel learning." In Advances in neural information processing systems, pp. 2339-2347. 2011.
Dürichen, Robert, Marco AF Pimentel, Lei Clifton, Achim Schweikard, and David A. Clifton. "Multitask Gaussian processes for multivariate physiological time-series analysis." IEEE Transactions on Biomedical Engineering 62, No. 1 (2015): 314-322.
Ghassemi, Marzyeh, Marco AF Pimentel, Tristan Naumann, Thomas Brennan, David A. Clifton, Peter Szolovits, and Mengling Feng. "A Multivariate Timeseries Modeling Approach to Severity of Illness Assessment and Forecasting in ICU with Sparse, Heterogeneous Clinical Data." In AAAI, pp. 446-453. 2015.
Gal, Yarin, and Richard Turner. "Improving the Gaussian process sparse spectrum approximation by representing uncertainty in frequency inputs." In International Conference on Machine Learning, pp. 655-664. 2015.
Rudin, Walter. Fourier analysis on groups. Courier Dover Publications, 2017.
Bishop, Christopher M. "Pattern Recognition and Machine Learning (Information Science and Statistics)." (2006).
Lee, Honglak, Alexis Battle, Rajat Raina, and Andrew Y. Ng. "Efficient sparse coding algorithms." In Advances in neural information processing systems, pp. 801-808. 2007.

* cited by examiner

POPULATION-LEVEL GAUSSIAN PROCESSES FOR CLINICAL TIME SERIES FORECASTING

This application is the U.S. National Phase application under 35 U.S.C. § 371 of International Application No. PCT/EP2020/057452, filed on 18 Mar. 2020, which claims the benefit of U.S. Provisional Applications 62/820,408, filed 19 Mar. 2019 and 62/943,955, filed 5 Dec. 2019. These applications are hereby incorporated by reference herein.

BACKGROUND

A provider may characterize a patient's health status by measuring clinical variables (e.g., heart rate, blood pressure, respiratory rate, etc.) over time to generate a clinical time series. To provide preventative care for the patient, the provider may utilize a mechanism configured to predict values for one or more of the patient's clinical variables. The prediction may be used to identify early warning signs related to the patient's health status. Subsequently, a clinical task may be performed based on the warning sign.

Conventional mechanisms that are configured to predict values for one or more of the patient's clinical variables may utilize machine learning. Some conventional mechanisms learn a patient-specific model using the test patient's existing clinical time series. However, patient specific models lack accuracy because they fail to extract patterns from the immense amount of available data collected from other patients (e.g., a training population). Thus, patient specific models do not use available data that could potentially benefit the prediction of the current patient. Other conventional mechanisms use a training population to generate a prediction model. However, conventional mechanisms that use the training population rely on parametric assumptions or post-processing using heuristics. Thus, these conventional mechanisms may lack accuracy. Accordingly, there is a need for a mechanism that is able to more accurately predict future values for the patient's clinical variable.

SUMMARY

According to an exemplary embodiment, a method may include collecting a multi-dimensional clinical time series for each of a plurality of training patients to generate a training population. The method further includes, training a machine learning algorithm using the training population. The method further includes, receiving measurement data corresponding to a test patient. The measurement data includes a multi-dimensional clinical time series for the test patient and wherein the test patient is not included in the plurality of training patients. The method further includes generating a prediction model for the test patient based on i) the measurement data corresponding to the test patient and ii) training the machine learning algorithm using the training population.

According to an exemplary embodiment, a monitoring device may include a communication interface and a processor configured to perform operations. The operations comprising receiving a set of data corresponding to a training population. The training population includes a multi-dimensional clinical time series for each of a plurality of training patients. The set of data is based on training a machine learning algorithm using the training population. The operations further comprising, receiving measurement data corresponding to a test patient. The measurement data includes a multi-dimensional clinical time series for the test patient. The test patient is not included in the plurality of training patients. The operations further comprising, generating a prediction model for the test patient based on i) the measurement data corresponding to the test patient and ii) the set of data corresponding to the training population.

According to an exemplary embodiment, a system includes a monitoring device and a server configured to perform operations. The operations comprising, collecting a multi-dimensional clinical time series for each of a plurality of training patients to generate a training population. The operations further comprising, training a machine learning algorithm using the training population. The operations further comprising, transmitting to the monitoring device a set of data corresponding to the training population. The set of data based on training the machine learning algorithm using the training population. The monitoring device configured to perform operations comprising, receiving the set of data corresponding to a training population. The operations further comprising, receiving measurement data corresponding to a test patient. The measurement data includes a multi-dimensional clinical time series for the test patient. The test patient is not included in the plurality of training patients. The operations further comprising, generating a prediction model for the test patient based on the measurement data corresponding to the test patient and the set of data corresponding to the training population.

DETAILED DESCRIPTION

Figure 1:
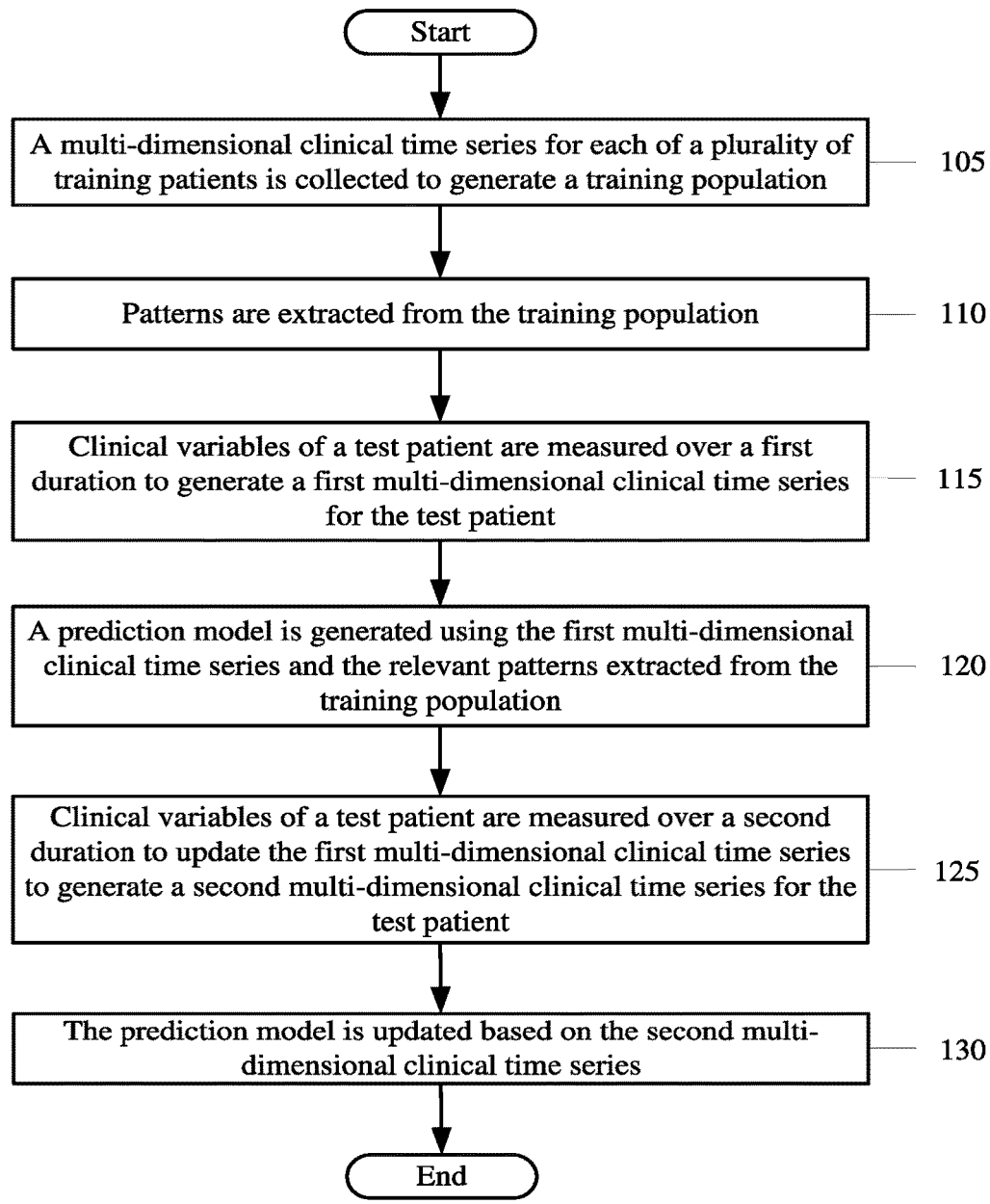
FIG. 1 shows a method for clinical time series forecasting according to various exemplary embodiments.

The exemplary embodiments may be further understood with reference to the following description and the appended drawings, wherein like elements are referred to with the same reference numerals. The exemplary embodiments relate to devices, systems and methods for predicting data relevant to a patient's health status that may be used to initiate a clinical task.

The exemplary embodiments are described with regard to collecting measurement data that characterizes a patient's health status. Throughout this description, the term "clinical variable" generally refers to a parameter that indicates the state of one or more body functions. To provide an example, a clinical variable may represent parameters such as, but not limited to, blood pressure, heart rate, temperature, respiratory rate, weight, pain level, blood glucose level, oxygen saturation, etc. However, any reference to a particular parameter being a clinical variable is only provided for illustrative purposes and is not intended to limit the scope of the term. A clinical variable may represent any parameter that indicates the state of one or more body functions.

The exemplary embodiments are described with regard to a patient's clinical variables being measured in a hospital. However, the exemplary embodiments are not limited to the measurement of a clinical variable being performed in any particular manner or in any particular setting. For example, the measurement of a clinical variable may be performed by a health care provider, the patient, a monitoring device inserted or coupled to the patient, a wearable device, a laboratory device, a device that tests bodily fluids and is used outside of the laboratory setting, a test strip or other material used for biological testing, a combination thereof, etc. Further, while the exemplary embodiments are described with regard to human patient, the exemplary embodiments may apply to any type of animal.

The patient's clinical variables may be measured over time. Throughout this description, a set of measurement data that represents measurements of a patient's clinical variable over time may be referred to as a "clinical time series." To provide an example, a clinical time series for heart rate may be (X1) beats per minute at a first time point, (X2) beats per minute at a second time point, (X3) beats per minute at a third time point, etc. Throughout this description, a set of data that includes two or more clinical time series for a particular patient may be referred to as a "multi-dimensional clinical time series." However, reference to the terms "clinical time series" and "multi-dimensional clinical time series" is only provided for illustrative purposes, different entities may refer to a similar concept by a different name.

The exemplary embodiments relate to machine learning. In a first aspect, the exemplary embodiments relate to training a machine learning algorithm using a multi-dimensional clinical time series from multiple patients. In a second aspect, the exemplary embodiments relate to forecasting future values for a patient's multi-dimensional clinical time series and/or at least one clinical variable using a prediction model that incorporates patterns learned from the training population. To differentiate between patients, a patient who is used for training the machine learning algorithm may be referred to as a "training patient" and a patient who is subject to the prediction model may be referred to as a "test patient."

Figure 2:
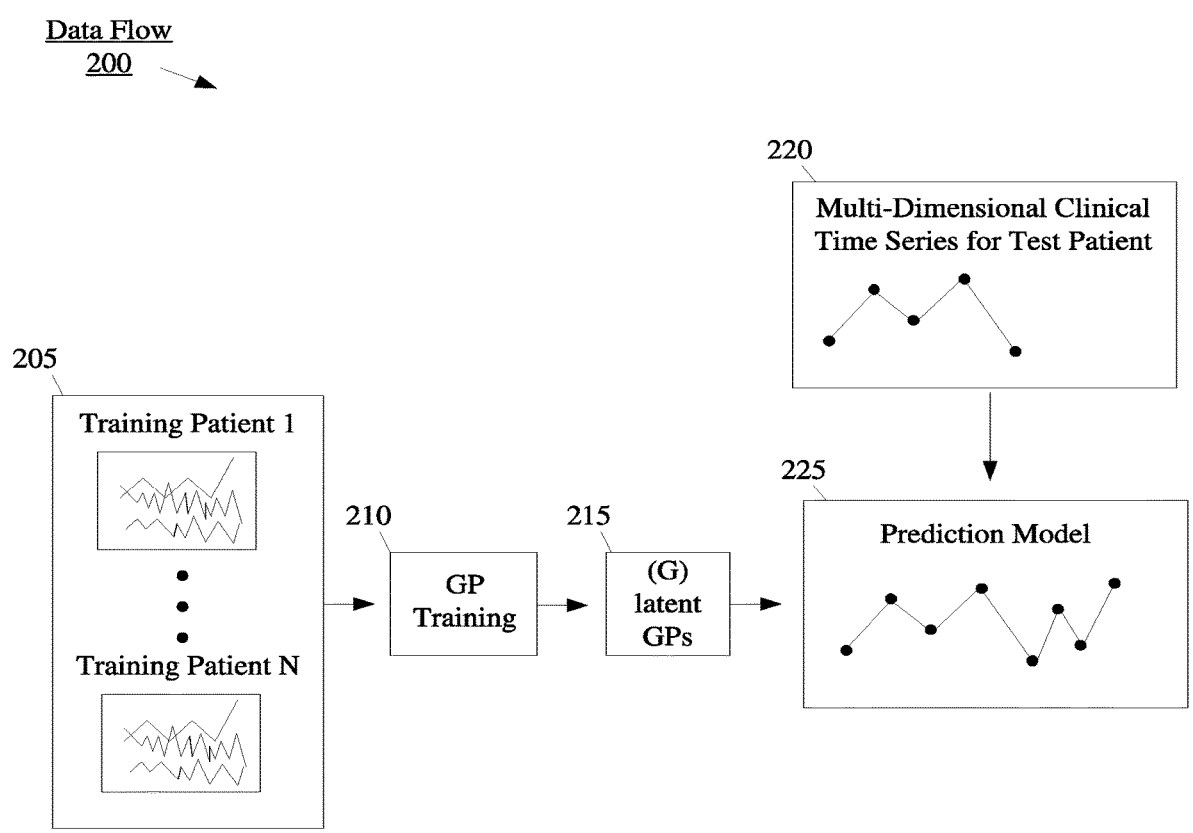
FIG. 2 shows a dataflow for clinical time series forecasting according to various exemplary embodiments.

FIG. 1 shows a method 100 for clinical time series forecasting according to various exemplary embodiments. The method 100 provides a general overview of how a multi-dimensional clinical time series for each of a plurality of training patients is used to forecast future values for one or more clinical time series of the test patient. FIG. 2 will be referenced during the description of FIG. 1 and is provided to illustrate a general overview of the dataflow that may occur during the method 100. Thus, FIG. 2 shows a dataflow 200 for clinical time series forecasting according to various exemplary embodiments. The examples provided in the method 100 and the data flow 200 are not intended to limit the scope of the exemplary embodiments in any way and are only intended to provide a general overview of how a prediction is made. Specific exemplary embodiments will be presented below.

In 105, a multi-dimensional clinical time series for each of a plurality of training patients is collected to generate a training population. The training population may include multi-dimensional clinical time series for N training patients. In the data flow 200, block 205 illustrates the multi-dimensional clinical time series for N training patients. For both training patient 1 and training patient N block 205 illustrates multiple line graphs to represent each patient's multi-dimensional clinical time series.

Returning to the method 100, in 110, patterns are extracted from the training population. To extract patterns from the training population a machine learning algorithm may be implemented. It may be assumed that the time series of each clinical variable for each training patient in the training population is the sparse linear combination of a set of latent Gaussian processes (GPs). Sharing latent GPs may account for the correlation between different clinical variables corresponding to the same training patient and across different training patients.

The multi-dimensional clinical time series of the training population may then be utilized to learn the set of latent GPs. For each latent GP, the kernel function may be parameterized by placing a prior on its corresponding frequencies and phases in the Fourier domain. Learning the posterior distribution of the frequencies and phases is equivalent to learning the kernel function. In the data flow 200, extracting patterns from the training population is represented by block 210 where GP training is performed. The GP training outputs G latent GPs in block 215.

Returning to the method 100, in 115, clinical variables of a test patient are measured over a first duration to generate a first multi-dimensional clinical time series for the test patient. In the data flow 200, block 220 illustrates the first multi-dimensional clinical time series for the test patient. In this example, the first multi-dimensional clinical time series is represented by a single line graph with five time points.

In 120, a prediction model is generated using the first multi-dimensional clinical time series and the relevant patterns extracted from the training population. The prediction model may forecast future values of the first multi-dimensional clinical time series.

To generate the prediction model, each clinical variable for the test patient may be modeled as a GP which is assumed to be the sparse linear combination of the set of latent GPs learned from the training population. The first multi-dimensional clinical time series of the test patient is then used to learn the GP of each clinical variable of the test patient by learning those sparse coefficients. The learned GP may then be used to forecast a future clinical time series for each clinical variable of the test patient.

In the data flow 200, the prediction model is shown in the block 225. In this example, the prediction model includes the five time points from the first multi-dimensional clinical time series and three predicted time points. Thus, using the first multi-dimensional clinical time series and the learned latent GPs, the exemplary embodiments may output predicted values for a multi-dimensional clinical time series and/or at least one clinical variable of the test patient.

Returning to the method 100, in 125, clinical variables of the test patient are measured over a second duration to update the first multi-dimensional clinical time series to generate a second multi-dimensional clinical time series. That is, after the prediction model is initially generated for the test patient in 120, the patient may still be monitored and thus, more measurement data is collected. This portion of the method 100 is not shown in the data flow 200.

In 130, the prediction model is updated based on the second multi-dimensional clinical time series. To update the prediction model, fit a GP model using the second multi-dimensional clinical time series and the learned posterior of sparse coefficients as the prior. Like in 120, the learned GP may be used to forecast a future time series for each clinical variable. Subsequently, the method 100 ends. This portion of the method 100 is not shown in the data flow 200.

In the method 100, the prediction model is updated once. During actual operation, updating the prediction model is a continuous process and may be initiated based on any appropriate factor. For example, updating the prediction model may be initiated based on a schedule, a timer, a predetermined condition, a predetermined number of measurements and/or observations, measurement data satisfying a predetermined threshold, user input, any combination thereof, etc.

Figure 3:
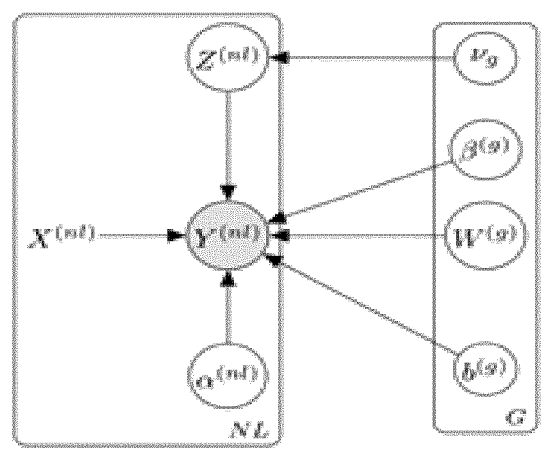
FIG. 3 shows a graphical model of a population-level Gaussian process according to various exemplary embodiments.

FIG. 3 shows a graphical model of a population-level Gaussian process according to various exemplary embodiments. The graphical mode includes G latent GPs. Each latent GP is parameterized by a frequency and phase sample in the Fourier domain. The clinical time series of each training patient is assumed to be the sparse linear combination of the G latent GPs.

As indicated above, to predict a future value for a test patient multi-dimensional clinical time series from training patients and a multi-dimensional clinical time series from the test patient may be used. To represent the training population, this example shows L-dimensional clinical time series from N training patients have been collected.

In this example, $Y^{(nl)} \in \mathbb{R}^{C_{nl}}$ represents $C_{nl}$ observations of the l-th clinical variable of the n-th training patient. $X^{(nl)} \in \mathbb{R}^{C_{nl} \times D}$ represents D-dimensional feature vector used to predict $Y^{(nl)}$. If only observed time points are available, then D=1 and $X^{(nl)}$ represents the collection of observed time points of the l-th clinical variable of the n-th training patient. To provide an example, a feature such as heart rate may be modelled based on its observed temporal dynamics. Different clinical variables of the same training patient are not required to share the same set of observed time points, e.g., $X^{(nl)} \neq X^{(nm)}$ ($l \neq m$) applies to various clinical variables corresponding to the same training patient. The time points of the clinical time series are also not required to be sampled at a consistent rate and may be sampled irregularly.

One clinical variable may be used to predict another clinical variable. For example, respiratory rate may correlate to a heart rate. Thus, if data other than time points are available as predictors, D>1 and $X^{(nl)}$ represents the collection of predictor variables.

To predict a future value for a test patient, a multi-dimensional clinical time series for the patient may also be used. To differentiate between the multi-dimensional clinical time series associated with a training patient and the multi-dimensional clinical time series associated with a training patient, the multi-dimensional clinical time series associated with a training patient may also be referred to as historical data. $Y_h^{(tl)} \in \mathbb{R}^{H_{tl}}$, $X_h^{(tl)} \in \mathbb{R}^{H_{tl} \times D}$ represents $H_{tl}$ observed values and the corresponding time points of the l-th clinical variable of the test patient t. The subscript h is used to denote these are encompassed within the historical data.

The exemplary embodiments relate to forecasting $Y_f^{(tl)} \in \mathbb{R}^{C_{tl}}$ (l=1, • • •, L), e.g., the future value of the test patient t's l-th clinical variable given $C_{tl}$ new time points $X_f^{(tl)} \in \mathbb{R}^{C_{tl} \times D}$. The subscript f is used to denote these are future values to be forecasted.

Returning to the graphical model shown in FIG. 3, at the training population level, assume there are G latent GPs, where the g-th latent GP is represented as:

$$f^{(g)}(x) \sim \mathcal{GP}(m^{(g)}(x), k^{(g)}(\cdot, \cdot))$$

Here, $f^{(g)}(x)$ is a population element used to reconstruct patient time series. $m^{(g)}(x)$ represents the mean function. Without strong prior knowledge, the prior may be set to 0 ($m^{(g)}(x)=0$).

$k^{(g)}(\cdot, \cdot)$ is the kernel function measuring the covariance between two function values, which are both random variables, generated from applying the function on two inputs, which may be represented as:

$$\text{cov}(f^{(g)}(x_1), f^{(g)}(x_2)) = k^{(g)}(x_1, x_2)$$

A person of ordinary skill in the art would understand that a GP defines a prior over functions and then updates the prior based on observed data. Some clinical variables may have a clinical time series that follows a multivariate Gaussian distribution, other clinical variables may exhibit non-Gaussian distributions (e.g., laboratory values tend to have heavy right-tailed distributions). The exemplary embodiments can be extended to these variables that exhibit non-Gaussian distributions by applying transformations (e.g., logarithmic or Box-Cox transforms) to make the features more Gaussian.

The exemplary embodiments relate to learning the kernel function $k^{(g)}(\cdot, \cdot)$ to each latent GP. Each latent GP may be parameterized using frequency and phase samples in the Fourier domain of the kernel function. This may be represented as:

$$f^{(g)}(x) = \sum_{m=1}^{M} \beta_m^{(g)} \cos(W_m^{(g)} x + b_m^{(g)})$$

Here, M is the number of frequency and phase samples in the Fourier domain. $W_m^{(g)}$ is the m-th frequency sample for $k^{(g)}(\cdot, \cdot)$, the kernel function of the g-th latent GP. $b_m^{(g)}$ is the m-th phase sample for $k^{(g)}(\cdot, \cdot)$ and $\beta_m^{(g)}$ is the m-th coefficient sample for $k^{(g)}(\cdot, \cdot)$. $W_m^{(g)}$, $b_m^{(g)}$ and $\beta_m^{(g)}$ are all illustrated on the right-hand side of the graphical model illustrated in FIG. 3.

A person of ordinary skill in the art would understand that the Fourier representations of GP may be derived from Bochner's theorem and the change of variable formula of integration. Learning the posterior of distribution of these frequencies, phases, and coefficients is equivalent to learning the kernel function.

To account for the correlation between different clinical variables within the same training patient and across different training patients, the clinical time series of each clinical variable of each training patient is generated from the sparse linear combination of G latent GPs. Compared to modeling different clinical variables of different training patients independently, the statistical strength can be shared across different clinical variables and different training patients. An example of observed data that may be generated may be represented as:

$$Y^{(nl)} = \sum_{g=1}^{G} (\alpha_g^{(nl)} Z_g^{(nl)}) f^{(g)}(X^{(nl)}) + \varepsilon^{(nl)}$$

$$= \Phi^{(nl)} (((\alpha^{(nl)} \circ Z^{(nl)}) \otimes 1_{M \times 1}) \circ \beta^{(1:G)}) + \varepsilon^{(nl)}$$

Here, $\Phi^{(nl)} = [\cos(X^{(nl)} W^{(1)} + b^{(1)} \otimes 1_{C_{nl} \times 1}), \cdot \cdot \cdot, \cos(X^{(nl)} W^{(G)} + b^{(G)} \otimes 1_{C_{nl} \times 1})] \in \mathbb{R}^{C_{nl} \times GM}$. In this example, $W^{(g)} \in \mathbb{R}^{D \times M}$ consists of M columns and each column contain a D-dimensional frequency sample and $b^{(g)} \in \mathbb{R}^{1 \times M}$ consists of M samples drawn from the phase distribution.

Further, $\beta^{(1:G)} \in \mathbb{R}^{GM \times 1}$ is the vertical concatenation of $\beta^{(1)}, \cdot \cdot \cdot, \beta^{(G)}$. The weight vector is $\alpha^{(nl)} \in \mathbb{R}^G$ and $Z^{(nl)} \in \{0,1\}^G$ is used to enforce the sparsity constraint. $\varepsilon^{(nl)} \in \mathbb{R}^{C_{nl}}$ is the Gaussian noise corrupting the observed data, the different elements of $\varepsilon^{(nl)}$ may have independent and identical distribution $\varepsilon_i^{(nl)} \sim \mathcal{N}(0, \sigma^{(nl)2})$. Hadamard (element-wise) product is represented by $\circ$ and the Kronecker product is represented by $\otimes$.

Accordingly, each training patient's clinical time a sparse linear combination of population dictionary Gaussian processes $f^{(g)}(X^{(nl)})$, g=1, . . . , G.

During training, the learning objective is to maximize the marginal likelihood of the observed data, max log $p(Y^{(1:N,1:L)})$. However, this is difficult to process due to the exponential complexity of integrating out those latent variables. Instead, the exemplary embodiments apply variational inference by introducing a variational distribution $q(h; \theta)$ over the collection of latent variables which is represented as:

$$h = \{Z^{(1:N,1:L)}, \alpha^{(1:N,1:L)}, W^{(1:G)}, b^{(1:G)}, \beta^{(1:G)}, v_{1:G}\}$$

Thus, the learning objective is to maximize the evidence lower bound (ELBO):

$$\max_{\theta} \mathbb{E}_{q(h;\theta)}[\log p(Y^{(1:N,1:L)} \mid h) + \log p(h) - \log q(h; \theta)]$$

The likelihood function $p(Y^{(1:N,1:L)}|h)$ can be derived from the generative process of $Y^{(nl)}$ which may be represented as:

$$\log p(Y^{(1:N,1:L)} \mid h) = \sum_{n=1}^{N} \sum_{l=1}^{L} \log \mathcal{N}(\Phi^{(nl)}(((\alpha^{(nl)} \circ Z^{(nl)}) \otimes 1_{M \times 1}) \circ \beta^{(1:G)}), \sigma^{(nl)2} \mathbb{I}_{C_{nl}})$$

The prior distribution of $Z^{(nl)}$ is the product of Bernoulli distributions, which may be represented as:

$$p(Z^{(nl)} \mid v_{1:G}) = \prod_{g=1}^{G} \text{Bernoulli}(v_g)$$

To enforce the sparsity constraint, we can use Beta prior on $v_g$ to encourage its density to be high near 0 and low elsewhere, such as $\tau_{v_{go}}=1$, $\gamma_{v_{go}}=5$, where $p(v_g)=\text{Beta}(\tau_{v_{go}}, \gamma_{v_{go}})$.

The prior distribution of $\alpha^{(nl)}$, $\beta^{(g)}$ and $W^{(g)}$ (shown in FIG. 3) are all fully-factorized Gaussians and the prior distribution of $b^{(g)}$ (also shown in FIG. 3) is uniform distribution. Thus, $p(\beta^{(1:G)}) = \prod_{g=1}^{G} \prod_{m=1}^{M} \mathcal{N}(\mu_{\beta_{gm}}, \sigma_{\beta_{gm}}^2)$, $p(\alpha^{(1:N,1:L)}) = \prod_{n=1}^{N} \prod_{l=1}^{L} \prod_{g=1}^{G} \mathcal{N}(\mu_{\alpha_{go}}^{(nl)}, \sigma_{\alpha_{go}}^{(nl)2})$, $p(W^{(1:G)}) = \prod_{g=1}^{G} \prod_{m=1}^{M} \prod_{d=1}^{D} \mathcal{N}(\mu_{W_{mdo}}^{(g)}, \sigma_{W_{mdo}}^{(g)2})$ and $p(b^{(1:G)}) = \prod_{=1}^{G} \prod_{m=1}^{M} U(t_{b_{mo}}, u_{b_{mo}})$.

Each latent variable may follow the same type of distribution as its prior. Thus, $q(\alpha^{(nl)}) = \prod_{g=1}^{G} \mathcal{N}(\mu_{\alpha_g}^{(nl)}, \sigma_{\alpha_g}^{(nl)2})$, $q(Z^{(nl)}) = \prod_{g=1}^{G} \text{Bernoulli}(\eta_g^{(nl)})$, $q(W^{(g)}) = \prod_{m=1}^{M} \prod_{d=1}^{D} \mathcal{N}(\mu_{W_{md}}^{(g)}, \sigma_{W_{md}}^{(g)2})$, $q(b^{(g)}) = \prod_{m=1}^{M} U(t_{b_m}^{(g)})$ an $q(\beta^{(g)}) = \prod_{m=1}^{M} \mathcal{N}(\mu_{\beta_{gm}}, \sigma_{\beta_{gm}}^2)$.

To derive the closed-form of the ELBO and maximize it with regard to variational parameters $\theta$ using gradient-based optimization algorithms, the optimal variational parameter is denoted as $\hat{\theta}$ and the number of latent GPs is denoted as $\hat{G}$. Constructing at least one clinical time series among NL time series in the training data the following equation may be utilized:

$$\hat{G} = \sum_{g=1}^{G} \mathbb{1}\left[\sum_{n=1}^{N} \sum_{l=1}^{L} \eta_g^{(nl)} > 0\right]$$

Since all G latent GPs might not be used, $\hat{G}$ could be smaller than G. The patterns learned from the training population are encoded in these $\hat{G}$ latent GPs. The posterior distribution may be represented as $q(W^{1:\hat{G}}, b^{(1:\hat{G})}, \beta^{(1:\hat{G})}; \hat{\theta})$.

After learning the above posterior distribution, it may be used as the prior of latent GPs when applying the prediction model (e.g., the prediction model in 120 of FIG. 1) using the historical data of the test patient $(X_h^{(t,1:L)}, Y_h^{(t,1:L)})$. As mentioned above, the learning objective is to maximize the ELBO of the marginal likelihood of $Y_h^{(t,1:L)}$ with regard to the test patient's sparse coefficient, which may be represented as $q(\alpha^{(t,1:L)}, Z^{(t,1:L)}; \theta^{(t)})$. Where $h^{(t)}$ to denote the collection of latent variables for the test patient. The learning objective may be achieved using the following equation:

$$\max_{\theta^{(t)}} \mathbb{E}_{q(h^{(t)};\hat{\theta}^{(t)})q(W^{(1:\hat{G})},b^{(1:\hat{G})},\beta^{(1:\hat{G})};\hat{\theta})}[\mathcal{L}_{likelihood} + \mathcal{L}_{prior} - \mathcal{L}_{variational}]$$

In the above equation, $\mathcal{L}_{likelihood} = \log p(Y_h^{(t,1:L)}|h^{(t)}, W^{1:\hat{G}}, b^{(1:\hat{G})}, \beta^{(1:\hat{G})})$, $\mathcal{L}_{prior} = \log q(W^{1:\hat{G}}, b^{(1:\hat{G})}, \beta^{(1:\hat{G})}; \hat{\theta}) + \log p(h^{(t)})$ and $\mathcal{L}_{variational} = \log q(W^{1:\hat{G}}, b^{(1:\hat{G})}, \beta^{(1:\hat{G})}; \hat{\theta}) + \log q(h^{(t)}, \theta^{(t)})$. The optimal parameter of the variational distribution is denoted as $\hat{\theta}^{(t)}$.

To forecast future time points of the multi-dimensional clinical time series for the test patient, the predictive distribution may be derived by integrating out latent variables. This is represented by the following equation:

$$p(Y_f^{(tl)}) = \mathbb{E}_{q(h^{(t)};\hat{\theta}^{(t)})q(W^{(1:\hat{G})},b^{(1:\hat{G})},\beta^{(1:\hat{G})};\hat{\theta})}[p(Y_f^{(tl)}, h^{(t)}, W^{(1:\hat{G})}, b^{(1:\hat{G})}, \beta^{(1:\hat{G})})]$$

The above equation may output the mean and standard deviation of the forecasted value.

As mentioned above in the method 100 of FIG. 1, the predictive model may be updated as more measurement data of the test patient is collected. As the number of observations increase for the test patient, the posterior $q(h^{(t)}; \theta^{(t)})$ can be updated by using the fitted $q(h^{(t)}; \hat{\theta}^{(t)})$ as prior when maximizing the ELBO of $p(Y_{new}^{(t,1:L)})$, the marginal likelihood of new observations.

Figure 4:
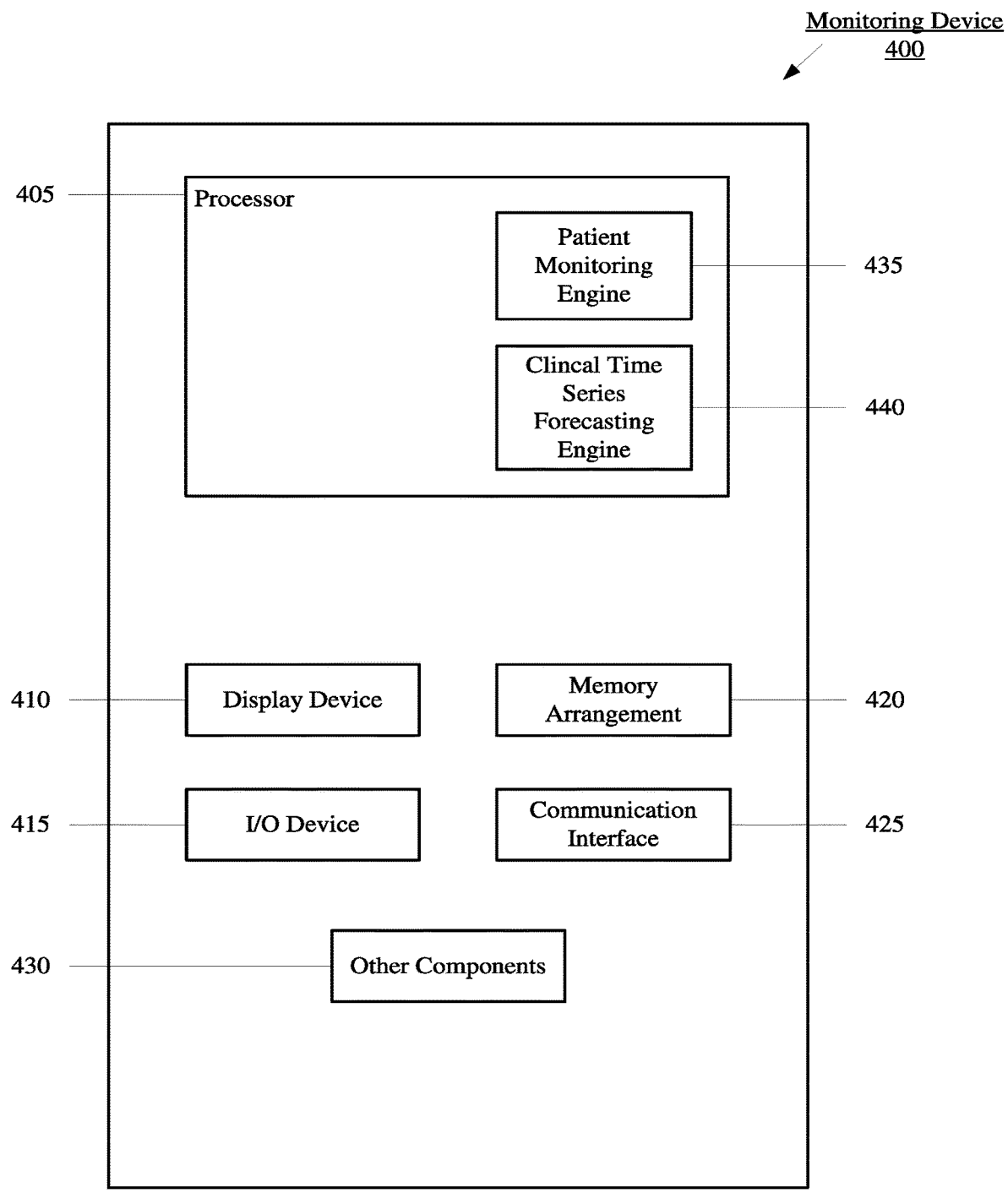
FIG. 4 shows a monitoring device that is configured to perform clinical time series forecasting according to various exemplary embodiments.

FIG. 4 shows a monitoring device 400 that is configured to perform clinical time series forecasting according to various exemplary embodiments. The monitoring device 400 may represent any electronic device that is configured with the hardware, software and/or firmware to receive data and process the data to output a prediction related to a one or more clinical time series. For example, the monitoring device may be a device configured for a clinical setting, a wearable device, a mobile phone, tablet computer, smartphone, an of Internet of Things (IoT) devices, etc.

The monitoring device 400 may include a processor 405, a display device 410, an input/output (I/O) device 415, a memory arrangement 420, a communication interface 425, and other components 430.

The display device 410 may be a hardware component configured to present a graphical display. The monitoring device 400 may include one or more display devices 410. For example, one display device 410 may be used to present a representation of the patient's real-time measurement data of one or more clinical variables and another display device 420 may be used to present a representation of measurement data that includes forecasted time points of one or more clinical variables. The I/O device 415 may be a hardware component that enables the user to enter inputs. The monitoring device 400 may include one or more I/O devices 415. For example, the display device 410 and the I/O device 415 may be integrated together such as a touchscreen. In another example, the I/O device 415 may be represented as one or more buttons. The communication interface 425 may be a hardware component configured to communicate with a network over a wireless or wired connection. The communication interface 425 may also be configured to communicate with other devices using a wired or wireless connection.

The processor 405 may be configured to execute a plurality of engines for the monitoring device 400. For example, the engines may include a patient monitoring engine 435 and a clinical time series forecasting engine 440. The patient monitoring engine 435 may manage how data (e.g., audio, video, text, graphics, etc.) is output by the monitoring device 400. This may include providing a graphical presentation of the patient's measurement data and omitting audio output when a predetermined condition is detected. The clinical time series forecasting engine 440 may implement the prediction model and manage how the results of the prediction model are output (e.g., audio, video, text, graphics, etc.).

The above referenced engines each being an application (e.g., a program) executed by the processor 405 is only exemplary. The functionality associated with the engines may also be represented as a separate incorporated component of the monitoring device 400 or may be a modular component coupled to monitoring device 400, e.g., an integrated circuit with or without firmware. For example, the integrated circuit may include input circuitry to receive signals and processing circuitry to process the signals and other information. The engines may also be embodied as one application or separate applications. In addition, the functionality described for the processor 405 may be split among two or more processors. The exemplary embodiments may be implemented in any of these or other configurations of a monitoring device.

The memory arrangement 430 may be a hardware component configured to store data related to operations performed by the monitoring device 400. The other components 430 may include, for example, an audio output device, ports to electronically connect to other devices, sensors to detect conditions of a patient, etc.

To provide an example of how the monitoring device 400 may be used by a provider consider the following exemplary scenario where a test patient is admitted to a hospital. Initially, the monitoring device 400 receives measurement data about the test patient (e.g., vital signs, laboratory results, etc.) The monitoring device 400 may receive the measurement data in any of a variety of different manners including, but not limited to, directly or indirectly from sensors coupled to the test patient, user input, directly or indirectly from an electronic medical record (EMR) platform, etc.

The monitoring device 400 (e.g., the patient monitoring engine 435) may process the measurement data and generate one or more clinical time series for the test patient. The monitoring device 400 may show a representation of the clinical time series.

In some embodiments, a system external to the monitoring device 400 may include various multi-dimensional clinical time series corresponding to training patients. For example, one or more servers may receive various multi-dimensional clinical time series corresponding to training patients and store this information in a database. The One or more of the servers may then perform training on the training population and provide to the monitoring device 400 the patterns and/or latent GPs extracted from the training population. However, this is merely provided for illustrative purposes and is not intended to limit the scope of the exemplary embodiments. A person of ordinary skill in the art would understand the hardware, software and/or firmware that may be implemented for the external system to perform these types of operations. In other embodiments, the monitoring device 400 may receive data representing the training population and extract patterns and/or latent GPs from the training population.

The monitoring device 400 (e.g., the clinical time series forecasting engine 440) may generate a prediction model using data corresponding to the test patient and the data corresponding to the training population. The monitoring device 400 may provide a display that includes a test patient's clinical time series and additional time points predicted by the prediction model. If the monitoring device 400 identifies a predetermined condition, the monitoring device 400 may output an alert that an abnormality has been detected and/or a clinical task should be performed. The monitoring device 400 may output the alert in any of a variety of different manners including, but not limited to, a graphical display on the display device 410, audio output, transmitting a message to another device (directly or indirectly) that is being monitored by the provider, etc. As more measurement data corresponding to the test patient is received by the monitoring device 400, the prediction model may be updated and thus, the monitoring device 400 may update the display that includes the test patient's clinical time series and additional time points predicted by the prediction model.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer implemented method, comprising:
collecting a multi-dimensional clinical time series for each of a plurality of training patients to generate a training population;
training a machine learning algorithm using the training population;
receiving measurement data corresponding to a test patient, wherein the measurement data includes a multi-dimensional clinical time series for the test patient and wherein the test patient is not included in the plurality of training patients; and
generating a prediction model for the test patient based on i) the measurement data corresponding to the test patient and ii) training the machine learning algorithm using the training population, wherein the multi-dimensional clinical time series for each of a plurality of training patients includes a plurality of clinical time series, each clinical time series includes a plurality of time points; and wherein each clinical time series is represented as a sparse linear combination of a set of latent gaussian processes and wherein training the machine learning algorithm using the training population includes learning each set of the latent gaussian processes.

2. The method of claim 1, further comprising:
determining one or more predicted values for a clinical variable of the test patient based on the prediction model;
identifying a predetermined condition based on the one or more predicted values; and
generating an indication corresponding to the predetermined condition.

3. The method of claim 2, wherein the clinical variable is one of heart rate, blood pressure, temperature or respiratory rate.

4. The method of claim 2, wherein the indication is one or more of audio output and a graphical display.

5. The method of claim 1, wherein the plurality of time points for at least one of the plurality of clinical time series occurs at an irregular frequency.

6. The method of claim 1, wherein a plurality of time points for a first clinical time series of the plurality of time series are not sampled at the same time as a plurality of time points for a second clinical time series of the plurality of time series.

7. The method of claim 1, wherein each latent gaussian process is parameterized by placing a prior on corresponding frequencies and phases in the Fourier domain.

8. The method of claim 1, further comprising:
receiving further measurement data corresponding to the test patient;
combining the measurement data corresponding to the test patient and the further measurement data corresponding to the test patient to generate an updated multi-dimensional clinical time series for the test patient; and
updating the prediction model using the updated multi-dimensional clinical time series for the test patient.

9. A monitoring device, comprising:
a communication interface; and
a processor configured to perform operations, the operations comprising:
receiving a set of data corresponding to a training population, wherein the training population includes a multi-dimensional clinical time series for each of a plurality of training patients,
wherein the set of data is based on training a machine learning algorithm using the training population, wherein the multi-dimensional clinical time series for each of a plurality of training patients includes a plurality of clinical time series, each clinical time series includes a plurality of time points, and wherein each clinical time series is represented as a sparse linear combination of a set of latent gaussian processes and wherein training the machine learning algorithm using the training population includes learning each set of the latent gaussian processes;

receiving measurement data corresponding to a test patient, wherein the measurement data includes a multi-dimensional clinical time series for the test patient and wherein the test patient is not included in the plurality of training patients; and
generating a prediction model for the test patient based on i) the measurement data corresponding to the test patient and ii) the set of data corresponding to the training population.

10. The monitoring device of claim 9, the operations further comprising:
determining one or more predicted values for a clinical variable of the test patient based on the prediction model;
identifying a predetermined condition based on the one or more predicted values; and
generating an indication corresponding to the predetermined condition.

11. The monitoring device of claim 9, further comprising an audio output device and wherein the indication corresponding to the predetermined condition is audio output.

12. The monitoring device of claim 9, further comprising a display device and wherein the indication corresponding to the predetermined condition is a graphic configured for display on the display device.

13. The monitoring device of claim 9, wherein the measurement data is received by the monitoring device via the communication interface from a sensor coupled to the test patient.

14. The monitoring device of claim 13, wherein the clinical variable is one of heart rate, blood pressure, temperature or respiratory rate.

15. The monitoring device of claim 9, wherein the plurality of time points for at least one of the plurality of clinical time series occurs at an irregular frequency.

16. The monitoring device of claim 9, wherein a plurality of time points for a first clinical time series of the plurality of time series are not sampled at the same time as a plurality of time points for a second clinical time series of the plurality of time series.

17. A system, comprising:
a monitoring device according to claim 11; and
a server configured to perform operations comprising:
collecting a multi-dimensional clinical time series for each of a plurality of training patients to generate a training population, wherein the multi-dimensional clinical time series for each of a plurality of training patients includes a plurality of clinical time series, each clinical time series includes a plurality of time points, and wherein each clinical time series is represented as a sparse linear combination of a set of latent gaussian processes and wherein training the machine learning algorithm using the training population includes learning each set of the latent gaussian processes,
training a machine learning algorithm using the training population, and
transmitting to the monitoring device a set of data corresponding to the training population, the set of data based on training the machine learning algorithm using the training population.

* * * * *